United States Patent

Hino et al.

[11] Patent Number: 5,504,542
[45] Date of Patent: Apr. 2, 1996

[54] STEREOSCOPIC RETINAL CAMERA HAVING JUDGING MECHANISM OF ALIGNMENT CONDITION

[75] Inventors: Toshiya Hino; Tsuguo Nanjo, both of Toyohashi; Tokio Ueno, Chiryu, all of Japan

[73] Assignee: Nidek Co., Ltd., Japan

[21] Appl. No.: 318,990

[22] Filed: Oct. 6, 1994

[30] Foreign Application Priority Data

| Oct. 29, 1993 | [JP] | Japan | 5-294410 |
| Oct. 29, 1993 | [JP] | Japan | 5-294411 |
| Nov. 30, 1993 | [JP] | Japan | 5-326181 |

[51] Int. Cl.$^6$ .................................................. A61B 3/14
[52] U.S. Cl. .................... 351/206; 351/208; 351/221
[58] Field of Search .................................. 351/206, 211, 351/221, 208

[56] References Cited

U.S. PATENT DOCUMENTS

| 4,678,297 | 7/1987 | Ishikawa et al. | 351/208 |
| 4,715,703 | 12/1987 | Cornsweet et al. | 351/208 |
| 5,120,122 | 6/1992 | McAdams | 351/206 |
| 5,141,303 | 8/1992 | Yamamoto et al. | 351/211 |
| 5,255,026 | 10/1993 | Arai et al. | 351/206 |
| 5,302,988 | 4/1994 | Nanjo | 351/206 |
| 5,371,557 | 12/1994 | Nanjho | 351/206 |
| 5,382,988 | 1/1995 | Nanjo | 351/206 |

FOREIGN PATENT DOCUMENTS

| 4-253838 | 9/1992 | Japan | 351/206 |
| 5-123299 | 5/1993 | Japan | 351/206 |
| 5-154111 | 6/1993 | Japan | 351/206 |
| 5-277078 | 10/1993 | Japan | 351/206 |
| 6-47002 | 2/1994 | Japan | 351/206 |

*Primary Examiner*—William L. Sikes
*Assistant Examiner*—James A. Dudek
*Attorney, Agent, or Firm*—Parkhurst, Wendel & Rossi

[57] ABSTRACT

In an stereoscopic retinal camera having a photographing optical system capable of photographing a pair of stereoscopic fundus images by dividing a light beam reflected by the fundus of an examinee's eye into two light beams through a two-hole diaphragm, provided are an illuminating optical system for illuminating the fundus of an examinee's eye, an observing optical system for observing the fundus illuminated by the illuminating optical system, a detecting optical system for detecting the luminous flux reflected by the fundus and then directed into the observing optical system, and based on the detected result by the detecting optical system, balance of video signal strength between a pair of the fundus images is judged thereby to take a stereoscopic photograph of the fundus.

9 Claims, 22 Drawing Sheets

Stereo luminous flux

Photographing area

71'b    71'a

72'b

72'a

STEREOSCOPIC RETINAL CAMERA HAVING JUDGING MECHANISM OF ALIGNMENT CONDITION

BACKGROUND OF THE INVENTION

1. Field of the Invention

The present invention relates to a stereoscopic retinal camera capable of photographing stereoscopically a fundus of an examinee's eye, and more particularly to a stereoscopic retinal camera comprising a judging mechanism to judge alignment condition of the camera with respect to the examinee's eye and capable of providing a right and a left pictures of uniform picture quality.

2. Description of Related Art

Conventionally, known are simultaneous stereoscopic retinal cameras capable of providing a pair of stereo images of a fundus of an examinee's eye by dividing a light beam reflected by the fundus into two light beams through a two-hole diaphragm and then photographing the divided light beams with right and left photographing optical systems respectively.

Alignment condition of the apparatus with respect to the eye has been judged by an examiner empirically while observing images of the fundus and the anterior surface of the eye through binocular eyepieces and a monitor.

Stereoscopic retinal cameras in the prior art are provided with a direct viewfinder for an observing optical system. Direct viewfinders of various type have been proposed, one of which is capable of observing a right and a left images of the fundus individually through each monocular eyepiece, another one of which is capable of observing the two images of the fundus arranged side by side by transmitting them inside the visual field of the monocular eyepiece, and last one of which is capable of observing the two images of the fundus through binocular eyepiece thereby to provide a stereoscopic vision.

The examiner carries out alignment operation of the apparatus while observing images of the fundus through any one of the direct viewfinders.

In fundus stereo photographing, uniformity in right and left picture images is important for diagnosis and analysis. In the apparatus in the prior art, a photographer has judged uniformity in right and left picture images, particularly uniformity of actual brightness in right and left images by directly observing balance of brightness of the two images.

The former alignment way has an advantage of capable of promptly and simply judging alignment condition, but has difficulty in judging it accurately because the observed images are constantly changing due to blinking or motion of the eye and so on. The examiner, particularly inexperienced, would therefore usually judge alignment to be achieved even when actual alignment is not proper. In the improper alignment condition, photographed picture images have unevenness in light quantity or flare light gotten therein, thereby not providing photographed images with high quality. Accordingly, there is a case where rephotographing of the images is required.

In the latter way with direct viewfinders, judgement on the balance of brightness between the two images is delicate, so that strict adjustment operation of the balance of brightness demands great skill and experience. Particularly, when photographing a fundus of an eye of an old person whose natural mydriasis is not sufficient, with a stereoscopic retinal camera without use of mydriasis, only one of right and left luminous flux is often eclipsed by the pupil of the eye. It is, accordingly, very difficult to adjust balance of brightness in the images.

SUMMARY OF THE INVENTION

The present invention has been made in view of the above circumstances and has an object to overcome the above problems and to provide a simultaneous stereoscopic retinal camera capable of easily and accurately judging alignment condition without demanding great skill and experience.

The second object of the present invention is providing a retinal camera capable of preventing photograph when alignment condition is not proper.

The third object of the present invention is providing a stereoscopic retinal camera capable of obtaining right and left picture images uniformly in picture quality, without requiring particular skill.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a stereoscopic retinal camera of this invention comprising a photographing optical system capable of photographing a pair of stereoscopic fundus images by dividing a light beam reflected by the fundus of an examinee's eye into two light beams through a two-hole diaphragm, the camera comprising, an illuminating optical system for illuminating the fundus of an examinee's eye, an observing optical system for observing the fundus illuminated by the illuminating optical system, a detecting optical system for detecting the luminous flux reflected by the fundus and then directed into the observing optical system, and judging means for judging balance of video signal strength between a pair of the fundus images based on the detected result by the detecting optical system.

According to the present invention, even in a stereoscopic retinal camera of synchronous photographing type which needs accurate alignment with the examinee's eye, it is possible to judge alignment condition properly for a short time. Therefore, use of the present invention will be effective in group schooling and so on for glaucoma.

It will be very convenient for diagnosis and analysis because unevenness of light quantity (video signal strength) does not appear in the right and the left picture images.

By detecting video signal strength of right and left images or balance of video signal strength between index images in the stereoscopic retinal camera, it is possible to achieve accurately alignment and to photograph the stereoscopic right and left images of the fundus with uniform brightness.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

FIG. 7 (b) is a schematic view of another area directing luminous flux for illuminating the fundus;

DETAILED DESCRIPTION OF THE PREFERRED EMBODIMENTS

A detailed description of preferred embodiments of a stereoscopic retinal camera embodying the present invention will now be given referring to the accompanying drawings.

Figure 1:
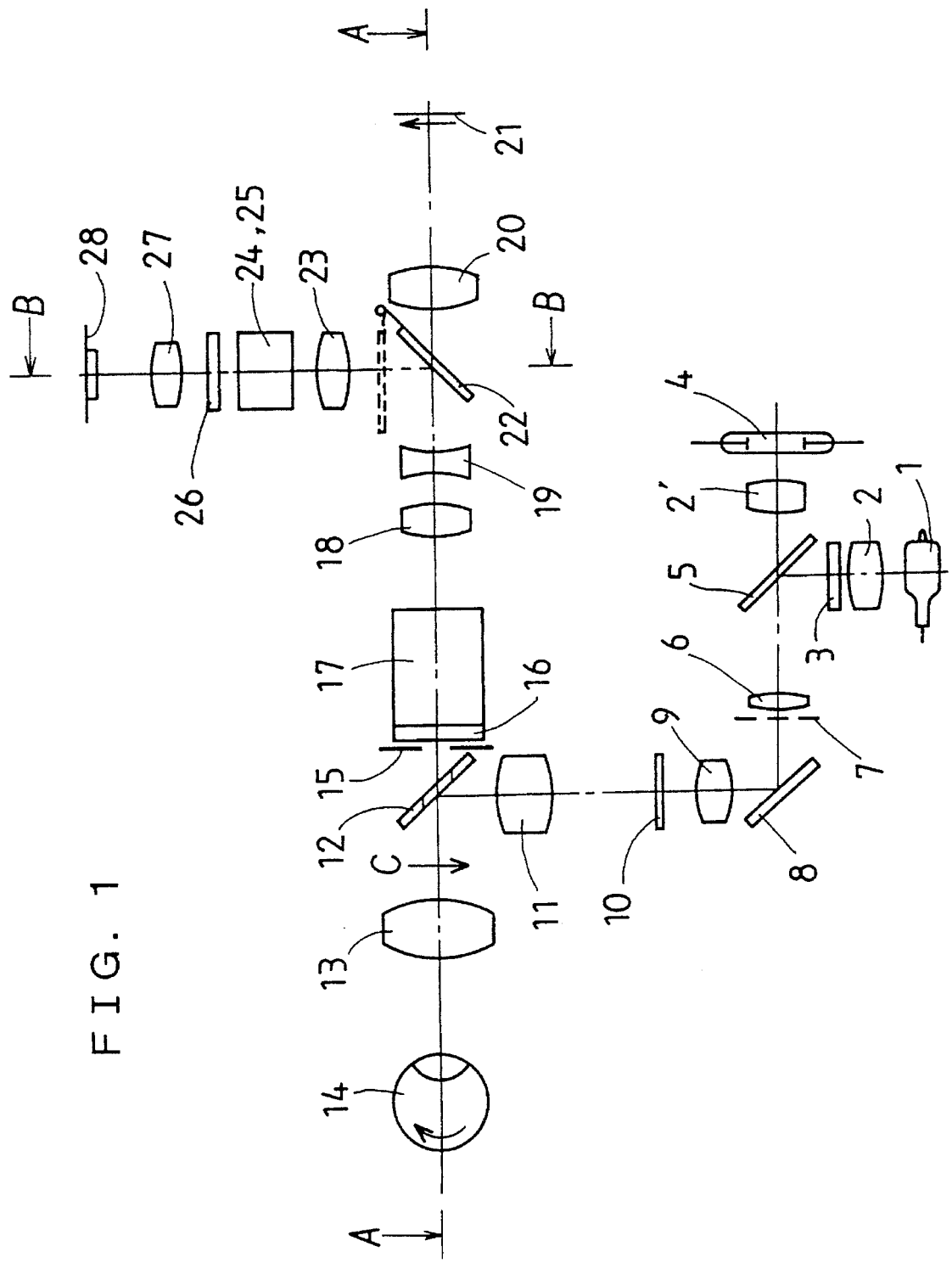
FIG. 1 is a schematic side view of the optical systems of a stereoscopic retinal camera in a first embodiment according to the present invention.
Figure 2:
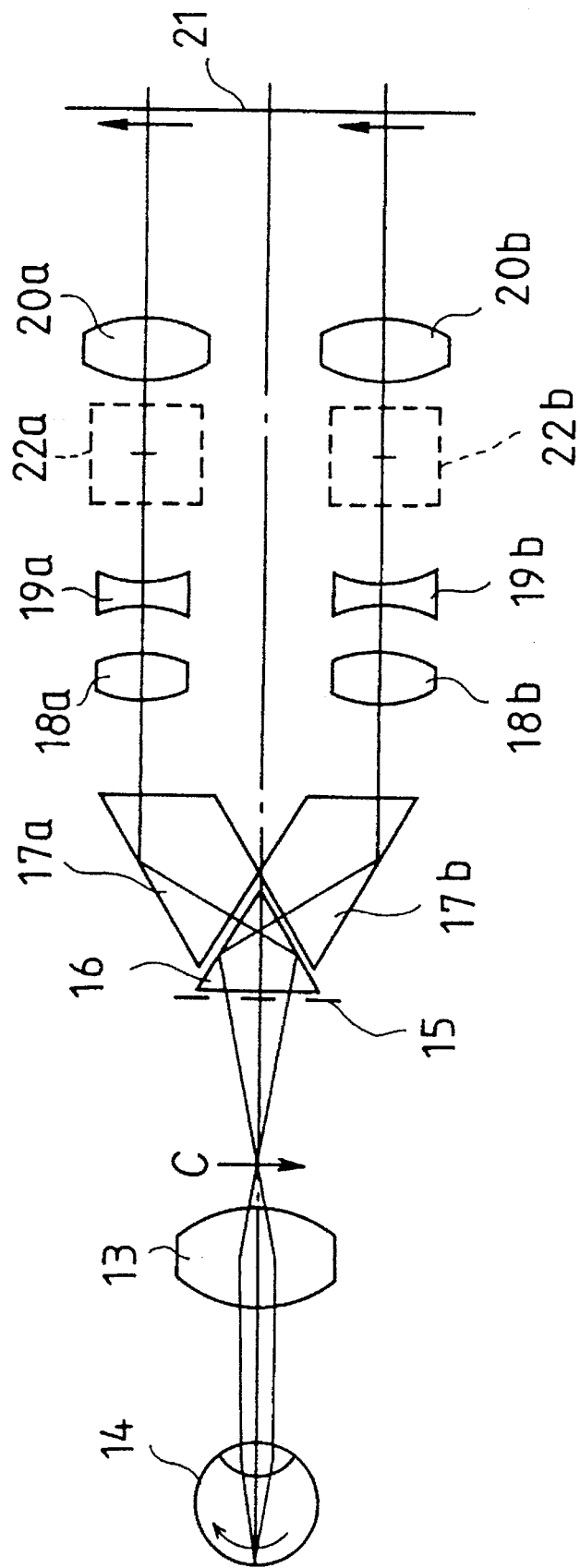
FIG. 2 is a schematic sectional view on line A—A of the photographing optical system of the stereoscopic retinal camera of FIG. 1.
Figure 3:
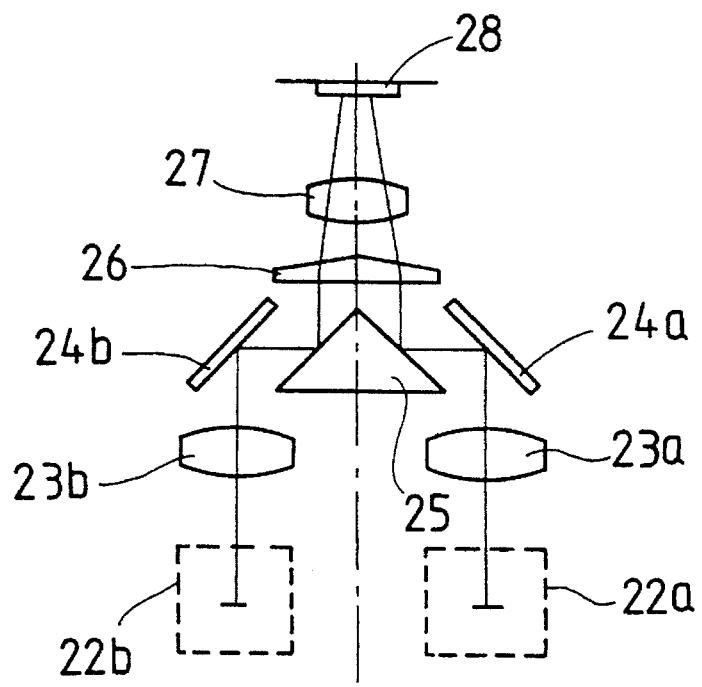
FIG. 3 is a schematic sectional view on line B—B of the observing optical system of the stereoscopic retinal camera of FIG. 1.

In FIG. 1, a stereoscopic retinal camera in a first embodiment of the present invention comprises an illuminating optical system, a photographing optical system and an observing optical system. FIG. 2 is a schematic sectional view on A—A line of the photographing optical system and FIG. 3 is a schematic sectional view on B—B line of the observing optical system.

Figure 4:
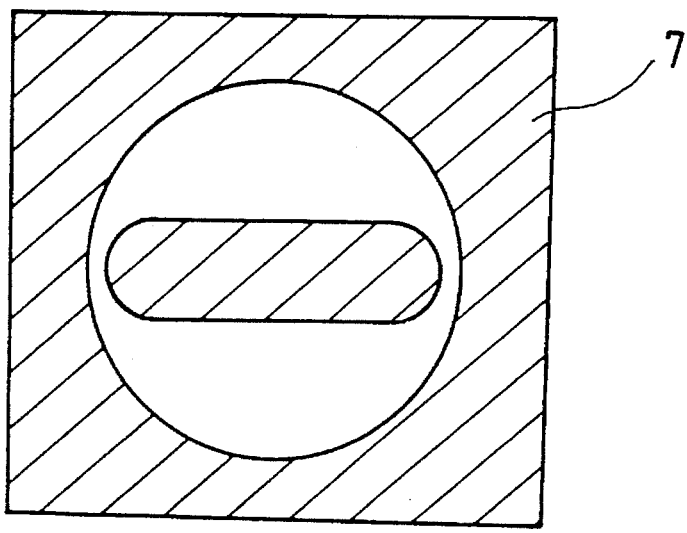
FIG. 4 is a schematic view of a ring slit 7 of FIG. 1.

The illuminating optical system is provided with a halogen lamp 1 which is a light source for supplying illumination light for observation, a condenser lens 2 for condensing the light beam emitted by the halogen lamp 1, an infrared filter 3 capable of transmitting only the infrared light by removing the visible light element of observing illumination light, a flash lamp 4 which is a light source for supplying photographing illumination light, and a condenser lens 2' for condensing the light beam emitted by the flash lamp 4. The infrared filter 3 is used in non-mydriasis photographing that utilizes the natural mydriasis of an examinee's eye in the dark. The illuminating optical system further comprises a beam splitter 5, a condenser lens 6, a ring slit 7 which is a ring type aperture diaphragm, the shape of which will be shown in FIG. 4, a mirror 8 for deflecting the light path, a relay lenses 9 and 11 of illumination optical system, an index plate 10 to eliminate the detrimental light and provided with a small black point on its center portion, a perforated mirror 12 provided centrally with an aperture to transmit the photographing light beam, and an objective lens 13.

The halogen lamp 1 for observation light and the flash lamp 4 for photographing light are disposed at a conjugate position with each other through the condenser lenses 2 and 2'. Both luminous flux emitted by the halogen lamp 1 and the flash lamp 4 respectively are compounded into the coaxial luminous flux through the beam splitter 5 to illuminate the ring slit 7.

The luminous flux transmitted through the ring slit 7 forms an intermediate image close to the aperture of the perforated mirror 12 through the relay lenses 9 and 11, and then is reflected by the ring-shaped mirror surface of the perforated mirror 12 thereby to be coaxial with the optical axis of the objective lens 13. The image of the ring slit 7 is formed close to the pupil of the examinee's eye 14 and diffuses in the inside of the eye to illuminate the fundus.

Figure 5:
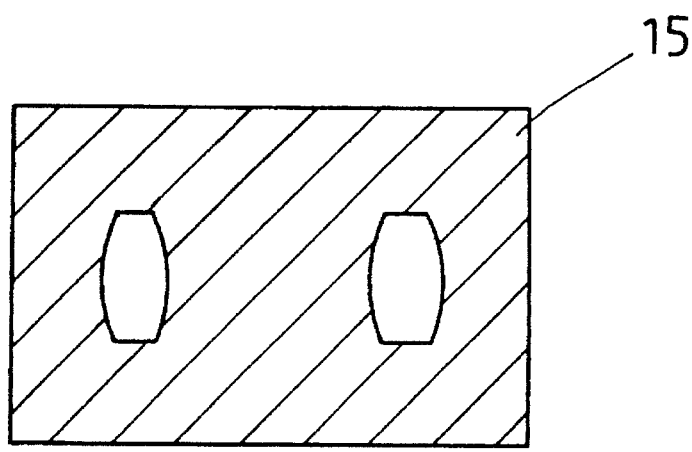
FIG. 5 is a schematic view of a two-hole diaphragm 15 of FIG. 1.

The photographing optical system comprises the objective lens 13 which is used in common in the illumination optical system, a two-hole diaphragm 15 for splitting the light beam into two right and left light beams for stereoscopic observation and photographing, the shape of which will be shown in FIG. 5, light beam splitting prisms 16 and 17 (17a, 17b), a relay lens 18 (18a, 18b), a focusing lens 19 (19a, 19b) movable along the light path of the photographing optical system so as to be adjusted according to the refracting power of the eye 14, an image forming lens 20 (20a, 20b) to form the image of the fundus on a film 21.

The light beam splitting prism 16 serves to interchanges a right light beam and a left light beam to prevent a stereoscopic image from becoming an inverted image, and the light beam splitting prism 17 serves to collimate the two light beams so that the collimated light beams pass along two parallel paths spaced at a predetermined interval.

Figure 6:
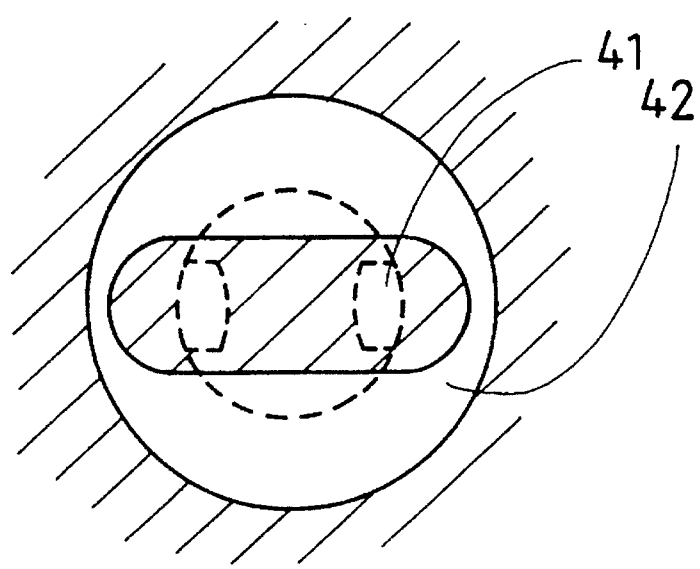
FIG. 6 is a schematic view of putting the ring slit 7 of FIG. 5 over the two-hole diaphragm 15 of FIG. 5 on the pupil.

The light beam reflected by the fundus of the eye 14 produces an inverted intermediate image at a point C through the crystalline lens of the eye 14 and the objective lens 13, and then passes through the opening of the perforated mirror 12, is split into two light beams through the two-hole diaphragm 15. The two-hole diaphragm 15 is disposed in a substantially conjugate relationship with respect to the pupil of the examinee's eye 14 through the objective lens 13, so that luminous flux separated on the pupil into a right and a left light beams for producing stereoscopic images are compounded at a point C, and then split again by the two-hole diaphragm 15. This means that size of photographing luminous flux is substantially determined according as the two-hole diaphragm 15. As described above, the image of the ring slit 7 of the illuminating optical system is formed close to the pupil on the examinee's eye 14. The ring slit 7 and the two-hole diaphragm 15 are disposed substantially conjugate with each other on the pupil. When the ring slit 7 is put over the two-hole diaphragm on the pupil, there appear images 41 of the apertures of the two-hole diaphragm 15 and an image 42 of a slit of the ring slit 7 as shown in FIG. 6.

Figure 7:
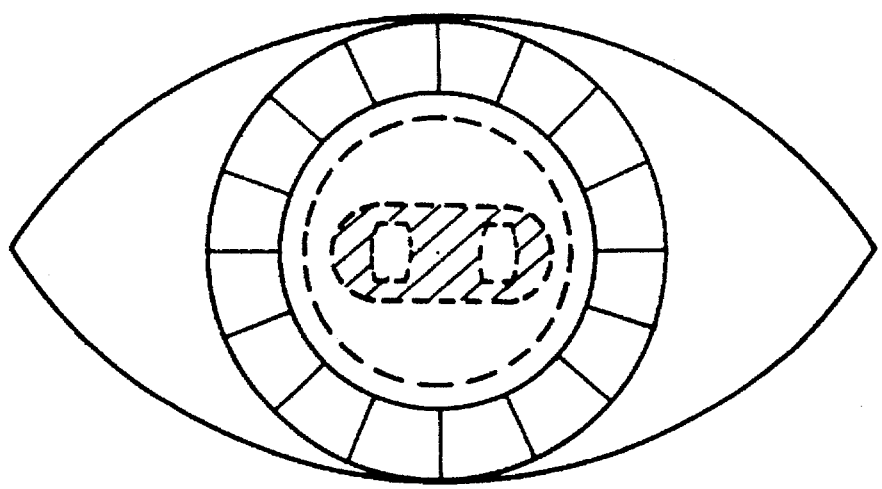
FIG. 7 (a) is a schematic view of an area directing luminous flux for illuminating the fundus.
Figure 7:
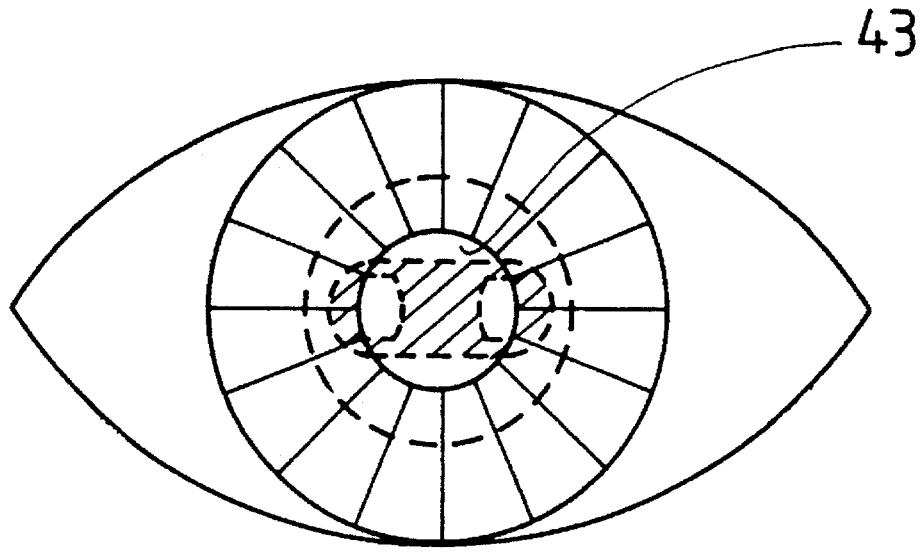

Luminous flux illuminating the fundus directed through the ring slit 7 is transmitted through an area without interfering with the two photographing luminous flux on the pupil, specifically, through mainly above and below the two luminous flux. The ring slit 7 in the present embodiment is designed so that the light quantity through the ring slit 7 may be introduced into the fundus of the eye 14 as much advantageously as the mydriatica diameter is wide, as shown in FIG. 7 (a). Even when the pupil diameter of the eye 14 is not enough wide and, accordingly, two photographing luminous flux 41 pass at just diametrical both ends of the pupil, the illuminating luminous flux can be directed through an area denoted by 43 in FIG. 7 (b) to the fundus.

In the photographing optical system, the light beam reflected by the fundus of the eye 14 is focused through the objective lens 13 at a point C in an inverted intermediate image, passes through the opening of the perforated mirror 12, and is split through the two-hole diaphragm 15 into two light beams. After that, the two light beams are collimated through the light splitting prisms 16, 17a and 17b, pass through the relay lenses 18a and 18b, the focusing lenses 19a and 19b and the image forming lenses 20a and 20b thereby to form right and left images on the film 21 respectively.

The return mirrors 22a and 22b are disposed at the time of observation on the illumination light path used in common by the observing optical system and the photographing optical system and, at the time of photographing, are turned up to a position indicated by a broken line in FIG. 1 to allow the illumination light emitted by the flash lamp 4 to pass to film 21.

As fundus illumination light, light invisible to the eye being examined is supplied at the time of non-mydriasis observation, which is allowed to pass through the infrared filter 3 that removes visible light element of light beam emitted by the lamp 4. At the time of photographing, a flash lamp 4 is caused to flash synchronously when the return mirrors 22 is swung upward out of the light path of the photographing optical system to allow the light beam to the film 21, so that light quantity necessary for instantaneously taking photos can fully be directed to the fundus.

The observing optical system uses in common the components between the objective lens 13 and the focusing lenses 19a and 19b with the photographing optical system.

The observing optical system further comprises, except the above components, return mirrors 22a and 22b, relay lenses 23a and 23b, mirrors 24a and 24b for deflecting luminous flux inwardly to shorten a distance between the two luminous flux, a triangle mirror 25 for deflecting the luminous flux upward, a deflection-angle prism 26 which serves to adjust each position of two right and left images, an image forming lens 27 of the observing optical system, and a TV camera image sensor 28 such as CCD and the like.

The observing light beam reflected by the fundus and passed through the components between the objective lens 13 and the focusing lenses 19a and 19b are reflected upward by the return mirrors 22a and 22b located on a solid line in the FIG. 1, and are transmitted through the relay lenses 23a and 23b, the mirrors 24a and 24b, the triangle mirror 25, the deflection-angle prism 26 and the image forming lens 27, thereby forming observation images on the image sensor 28 which is disposed in a substantially conjugate relation with the film 21.

Figure 8:
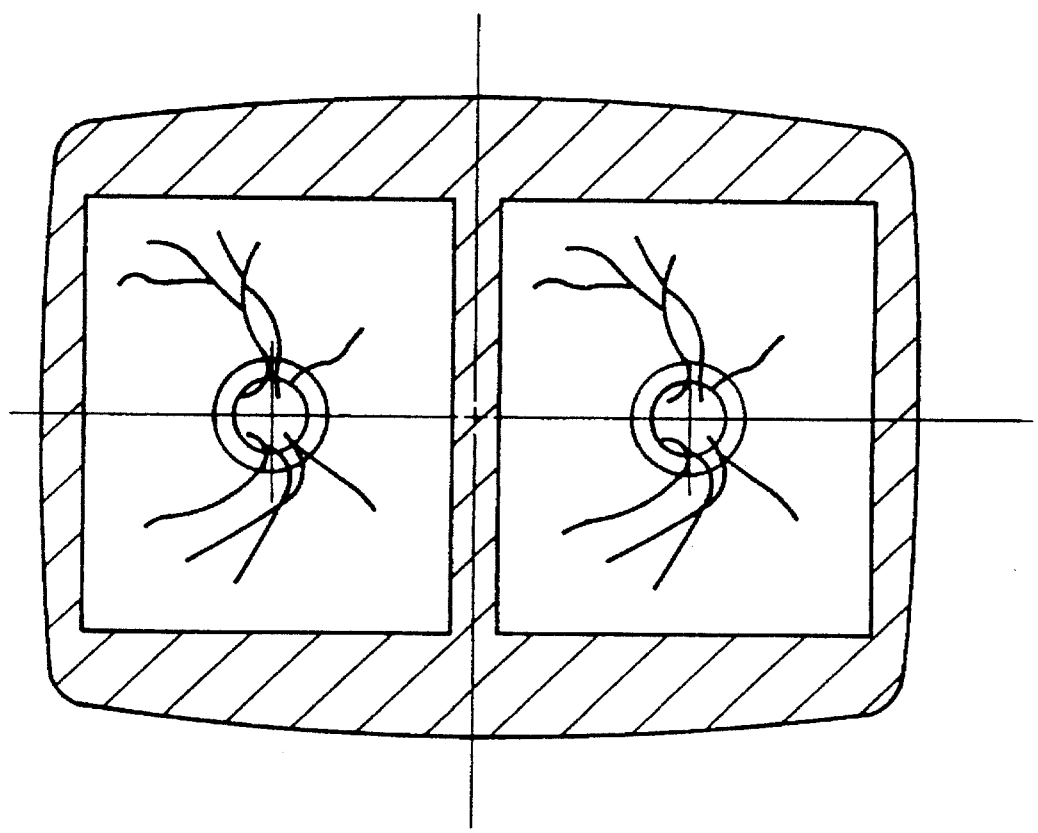
FIG. 8 is a schematic view of an example of the images of the fundus photographed with a TV camera and displayed on a TV monitor screen.

FIG. 8 shows an example of TV monitor screen for displaying a pair of picture images taken by TV camera, which are to be used for stereoscopic photographing.

The present embodiment employs a TV camera and a TV monitor, which may be modified to, for example, exclusive TV cameras for right and left respective images, only a TV monitor shared in common through an image composing circuit, or a plurality of TV monitors.

Figure 9:
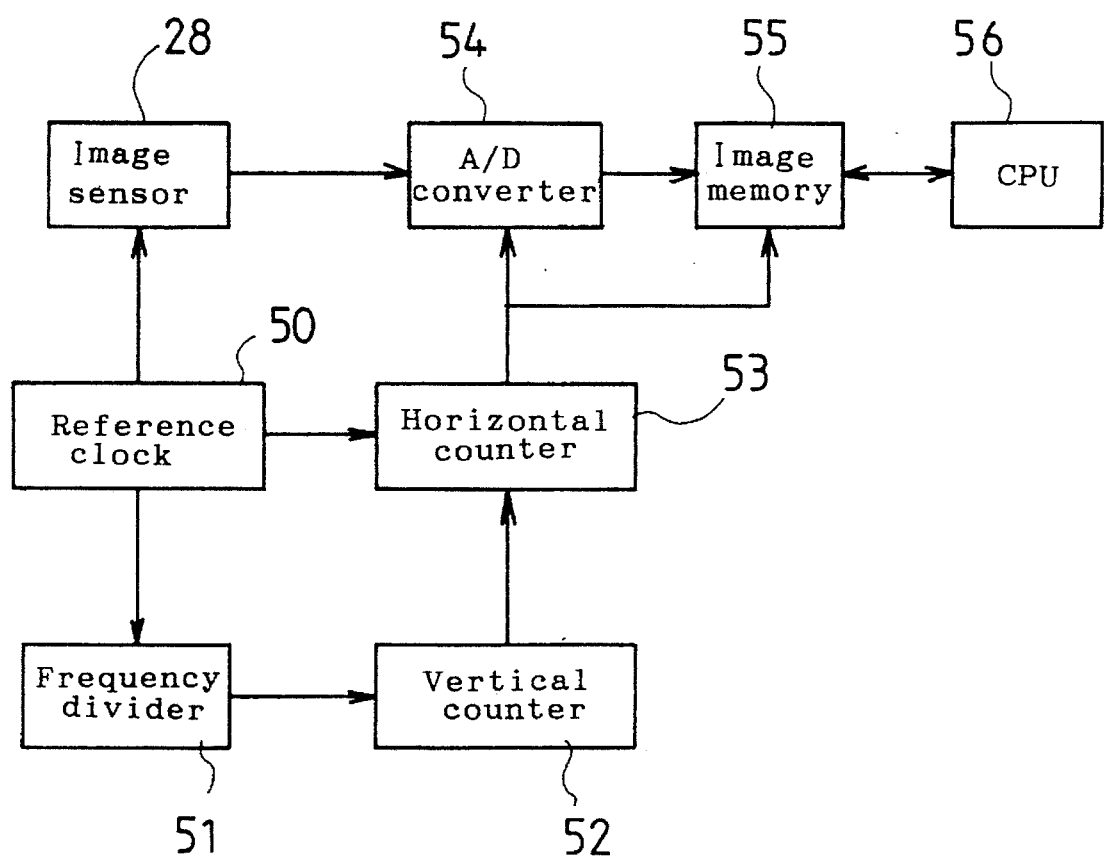
FIG. 9 is a block diagram of explaining an alignment judging mechanism.

FIG. 9 shows a block diagram of alignment judging mechanism, which comprises a reference clock generator 50, a frequency divider 51 for generating a vertical synchronous signal, a vertical counter 52, and a horizontal counter 53. When the vertical scanning comes to a position apart by a predetermined distance from a vertical scanning start point, the vertical counter 52 transmits a count starting signal to the horizontal counter 53 to start horizontal scanning. It is preferable for alignment judgement to use a horizontal scanning line across a macular portion.

Image video signals generated at the image sensor 28 are converted to digital signals through an A/D converter 54 while synchronizing with signals of the horizontal counter 53, and then is fed to an image memory 55. CPU 56 controls the memory 55 to add accumulatively and store each video signal of the right and left photographed picture images on the horizontal scanning line.

Figure 10:
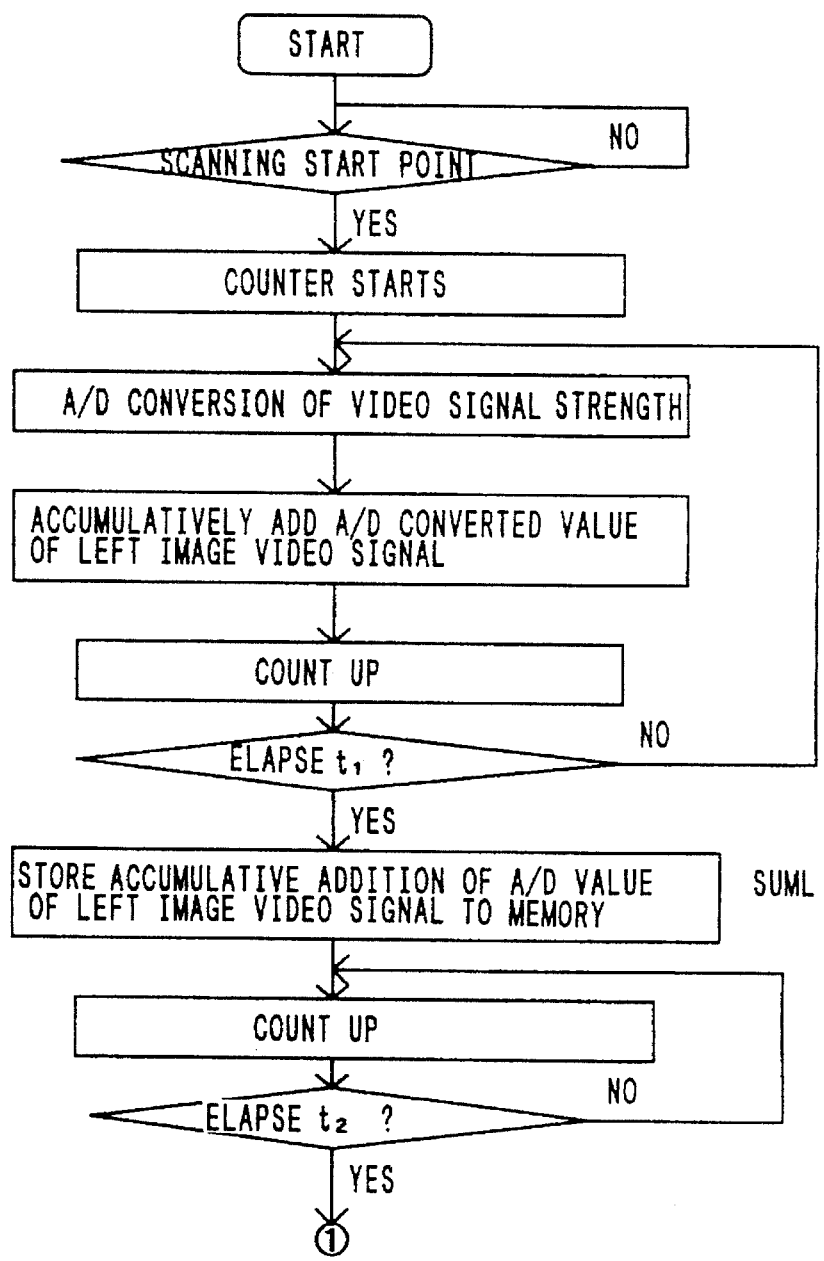
FIG. 10 is a flow chart of explaining an alignment operation, which is continued to FIG. 11.
Figure 11:
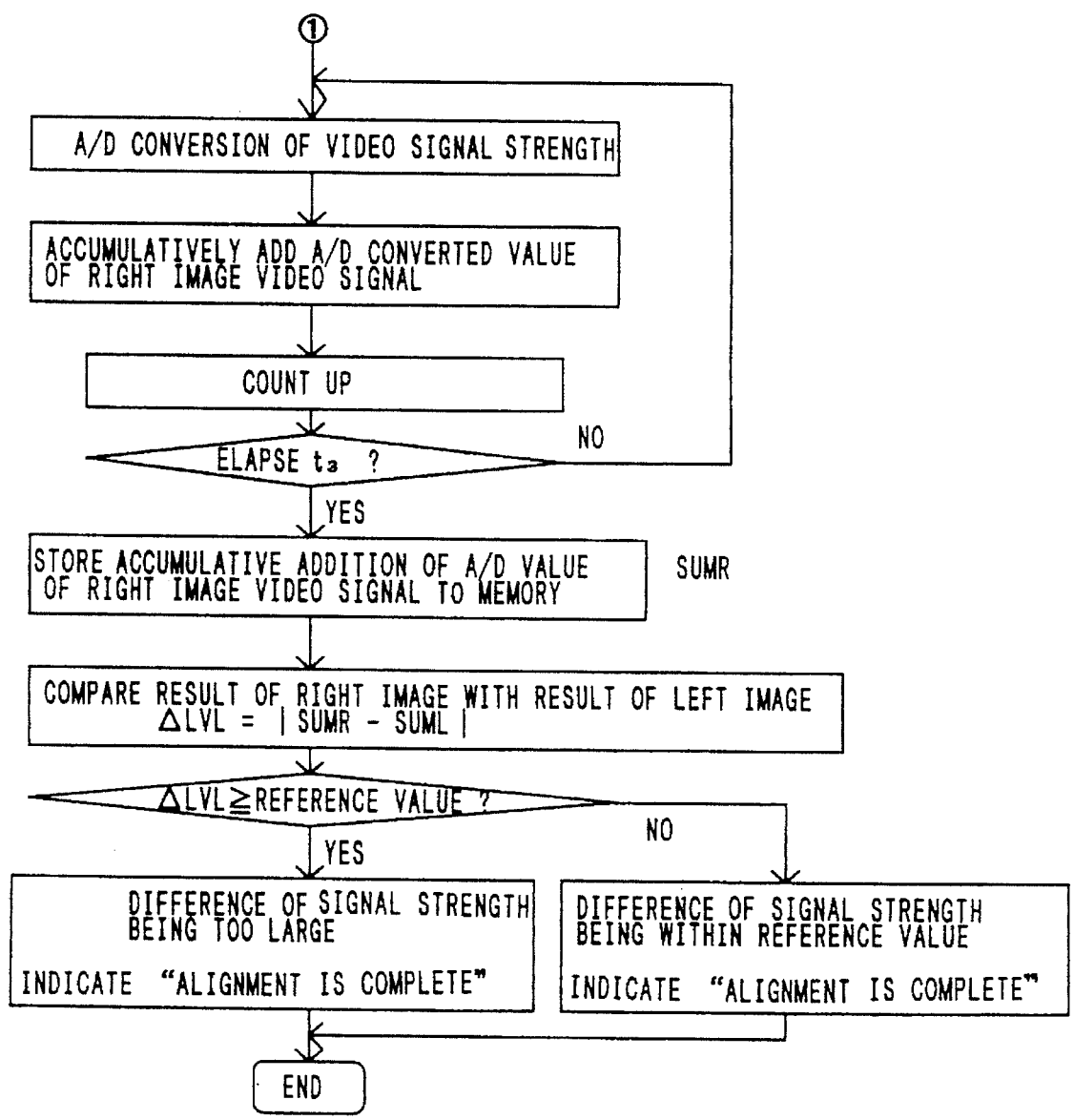
FIG. 11 is a flow chart of explaining an alignment operation.

In the stereoscopic retinal camera of the present embodiment constructed as above, alignment operation thereof will be described hereinafter referring to FIG. 10 and FIG. 11.

The optical systems, which are provided in a casing of the camera, are put on an operation table movable on a fixed table by a sliding mechanism. The head of an examinee first is held fixedly on a head support mounted to the fixed table. The halogen lamp 1 which is a light source to supply observing illumination light is turned on to illuminate the eye 14 of the examinee. While observing observation picture images displayed on the TV monitor (referring to FIG. 8), the photographer (examiner) moves the operation table in back and before, right and left, and up and down directions with respect to the examinee's eye so that the camera and the eye are aligned in a desired positional relation.

Figure 12:
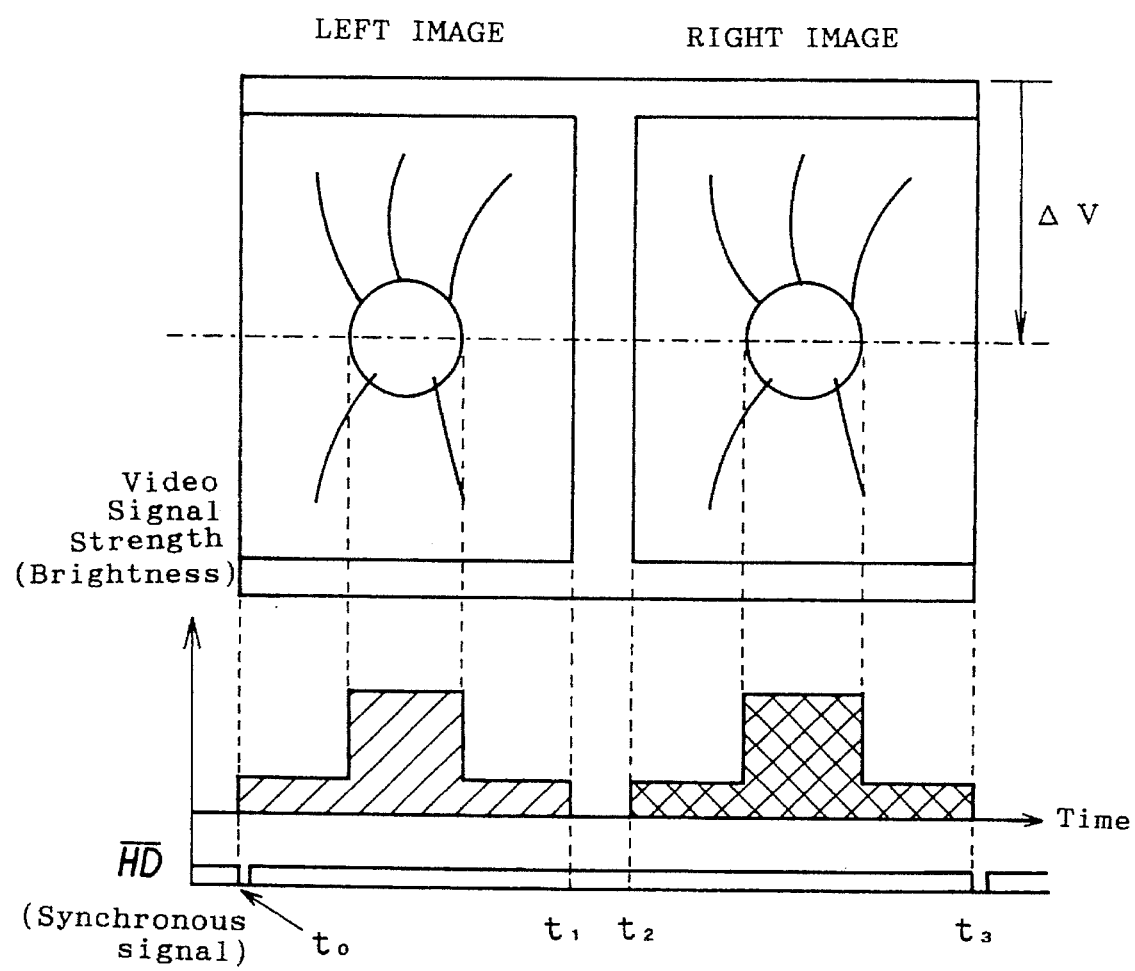
FIG. 12 is a diagrammatic view of explaining an alignment judgement.

Now, judgement of alignment condition will be performed as follows, referring to FIG. 12. In FIG. 12, upper schematic diagrams show an example of photographed images of the image sensor 28, a right image of which is formed through a right optical system and a left image of which is formed through a left optical system.

The judging operation begins by confirming the initial portion of scanning signal of the image sensor 28. The vertical counter 52 is then operated to count vertical clock of $\Delta V$. When the scanning signal reaches $\Delta V$, the horizontal counter 53 is started simultaneously with horizontal synchronous signals. Synchronizing with the horizontal counter 53, video signals in the form of analog signal are converted into digital signals through the A/D converter 54, and then the CPU 56 controls the memory 55 to accumulate the converted digital signals.

In FIG. 12, lower diagrams graphically show video signals on a horizontal scanning line which is deviated by $\Delta V$ from the vertical scanning start point (the upper end in FIG. 12). In a horizontal scanning period $(t_0-t_3)$, $t_0-t_1$ shows an input image video signal transmitted through the left optical system, $t_1-t_2$ shows a separate range between right and left images, and $t_2-t_3$ shows an input image video signal transmitted through the right optical system.

The memory 55 stores total amount of accumulative addition in a term of $t_0-t_1$ by horizontal scanning for video signal strength amount of the left optical system (SUML). Then, accumulative addition buffer stored in the memory 55 is cleared and the horizontal clock converts the video signal strength in a term of $t_2-t_3$ through the A/D converter to sequentially accumulatively add. The total amount of accumulative addition is stored in the memory 55 (SUMR).

CPU 56 judges then whether the difference of accumulated signal strength of the right and the left images (|SUMR-SUML|) is within a predetermined value (acceptable value). More specifically, CPU 56 judges alignment to be proper when the difference value is within a predetermined value, alternatively, alignment to be improper when the difference value exceeds the predetermined value.

Figure 13:
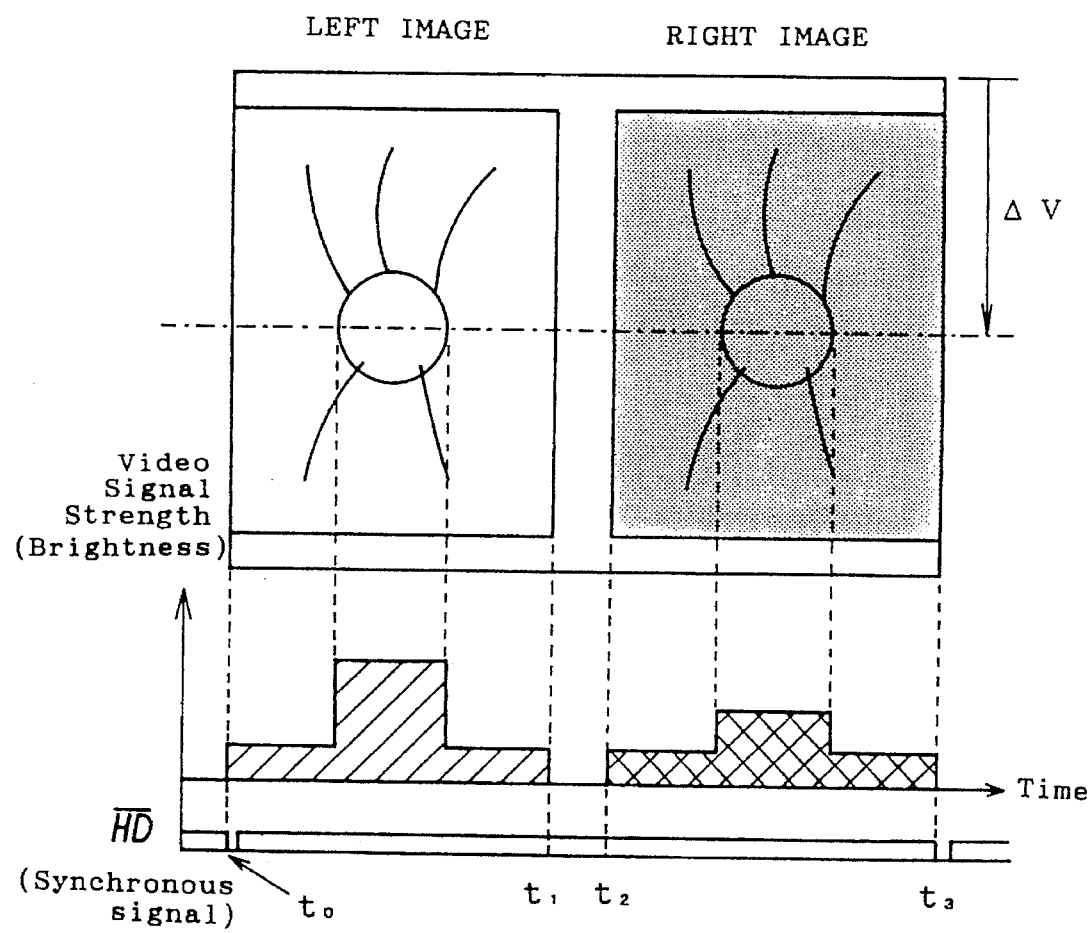
FIG. 13 is a diagrammatic view of showing an example of improper alignment.

FIG. 13 is an example of photographed picture images in a case of improper alignment of photographing optical axis with respect to an examinee's eye, whereby obvious difference of video signal strength is caused in the right and left optical systems. Thus, it causes a large difference value between accumulative additions of video signal in the right and left optical systems, so that alignment condition is judged to be improper.

Figure 14:
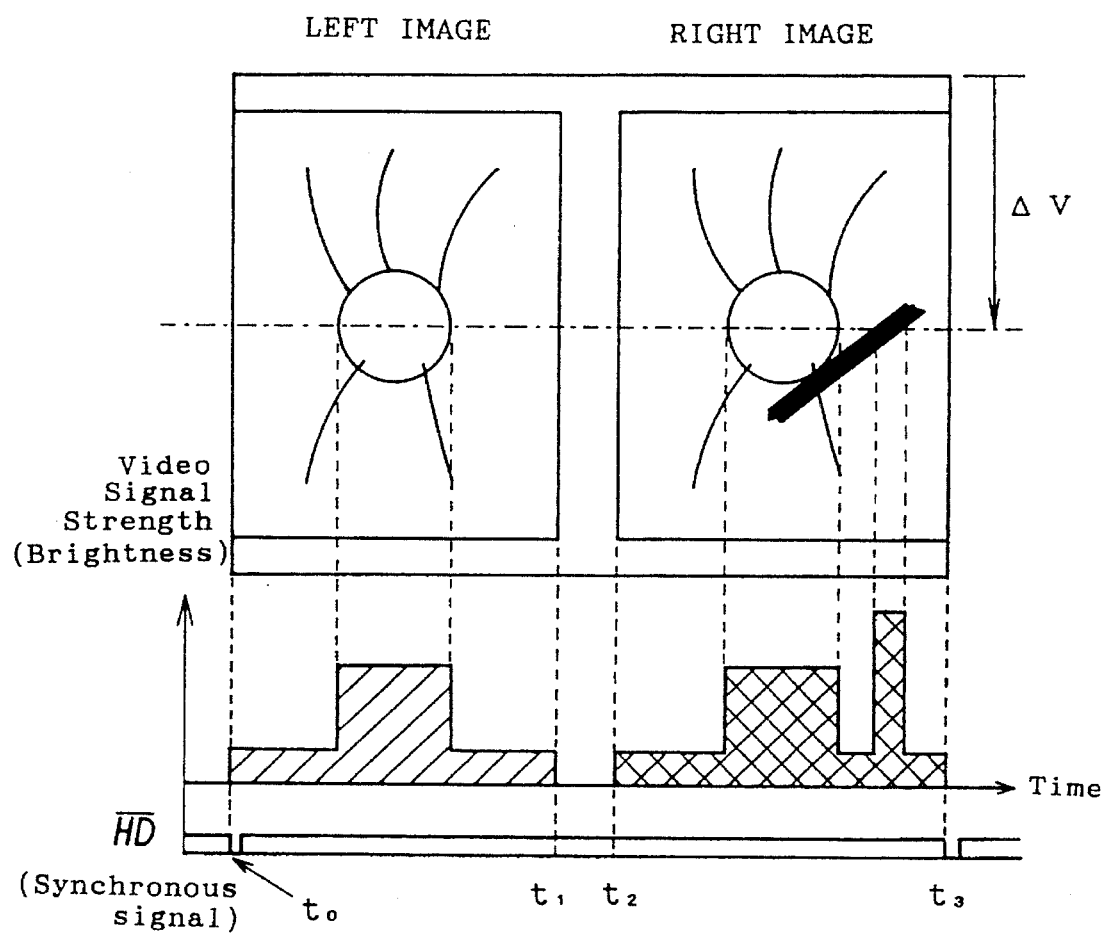
FIG. 14 is a diagrammatic view of showing another example of improper alignment.

FIG. 14 is another example of photographed picture images in a case of improper alignment, whereby producing flare of external disturbance light in the right optical system. Also in this case, alignment is detected to be improper due to that the accumulative addition of video signal strength of the right optical system is obviously larger than that of left optical system.

The alignment condition judged as above is informed the examiner with a TV monitor or an alarm or the like.

After alignment (and focusing), when a photographing button not shown in the figure is depressed, the return mirror 22 turns up to a position indicated by a broken line and, simultaneously, the xenon flash lamp 4 flashes to illuminate the fundus with the light necessary for photographing images on the film 21.

It is possible to adapt the return mirror 22 so as not to move when judging a signal indicates improper alignment, even if a trigger switch is depressed. Instead of detecting accumulated video signals on only a scanning line, it is possible to judge alignment by comparing accumulated video signals on a plurality of scanning lines respectively.

Figure 15:
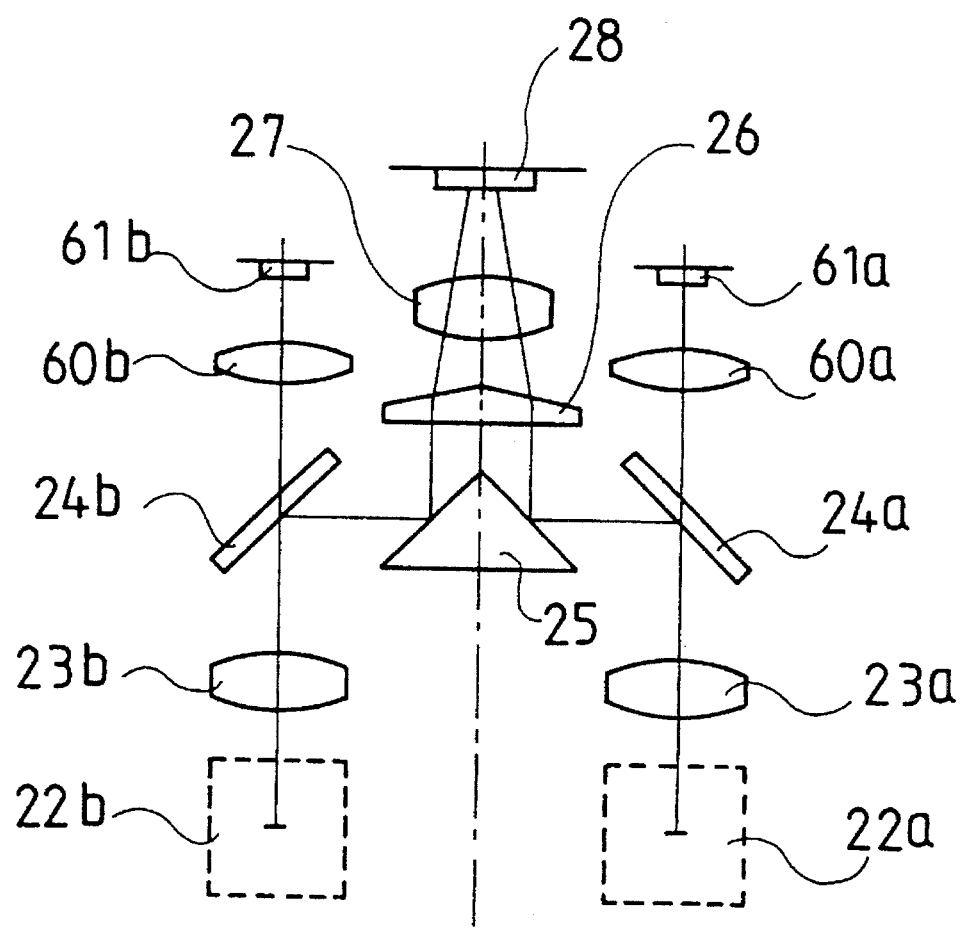
FIG. 15 is a schematic side view of the observing optical system of the stereoscopic retinal camera in a second embodiment according to the present invention.

In a second embodiment according to the present invention, a stereoscopic retinal camera comprises an observing optical system different from that of the first embodiment, which is shown in FIG. 15. The observing optical system comprises the similar components between the return mirror 22 and the image sensor 28 to that of FIG. 3, and further comprises a condenser lense 60 (60a, 60b) and a light receiving element 61 (61a, 61b). Additionally, the half mirror 24 (24a, 24b) in the second embodiment serves to deflect luminous flux inwardly to shorten a distance therebetween, and to selectively partially transmit luminous flux reflected by the fundus. Luminous flux transmitted through each of the half mirrors 24 (24a, 24b) is condensed through the condensing lens 60 (60a, 60b) to be directed to the light receiving element 61 (61a, 61b), and each video signal strength of right and left images are detected then.

The half mirrors 24a and 24b are disposed in the observing optical system in the second embodiment, and may be disposed in the photographing optical system.

Alignment operation in the second embodiment will be described as follows, but similar operation to the first embodiment is omitted from the description.

Figure 16:
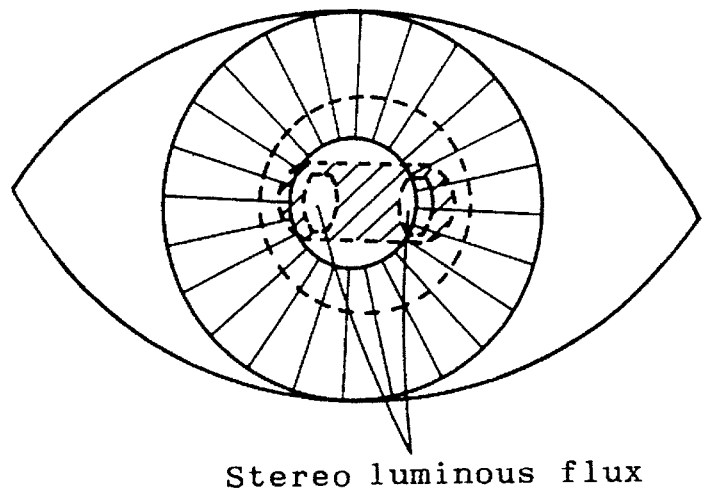
FIG. 16 (a) and (b) are schematic views of showing deviation of photographing optical axis.
Figure 16:
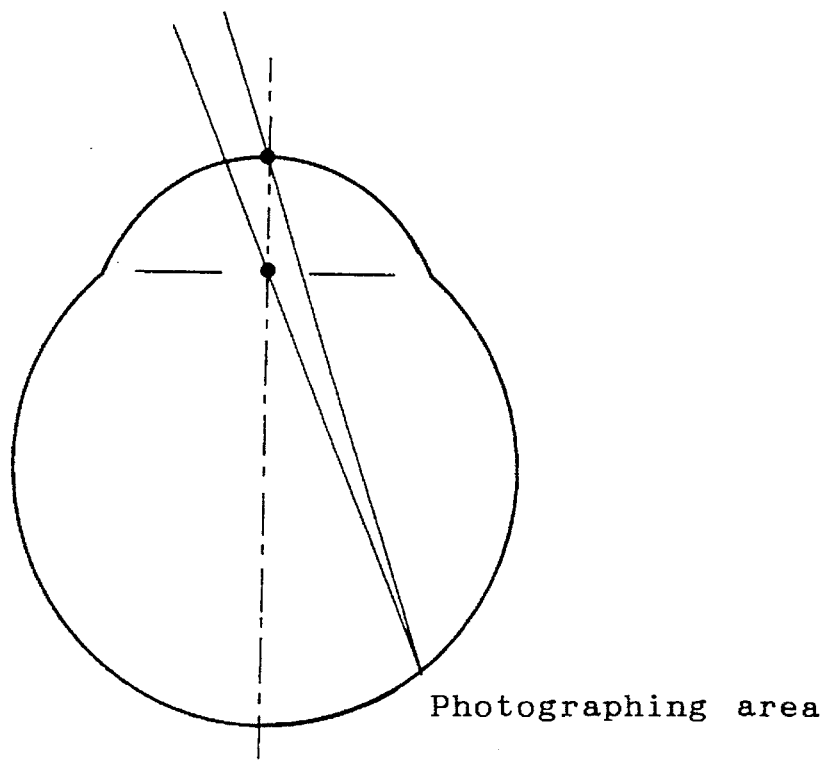
Figure 18:
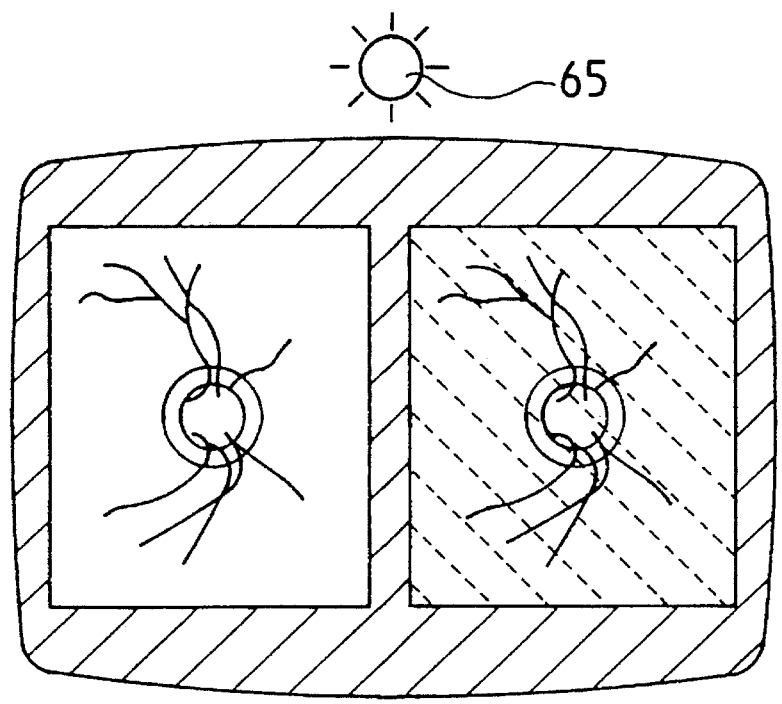
FIG. 18 is a schematic view of showing an example of TV monitor when luminous flux for illuminating the fundus is eclipsed and a lamp for alignment.
Figure 19:
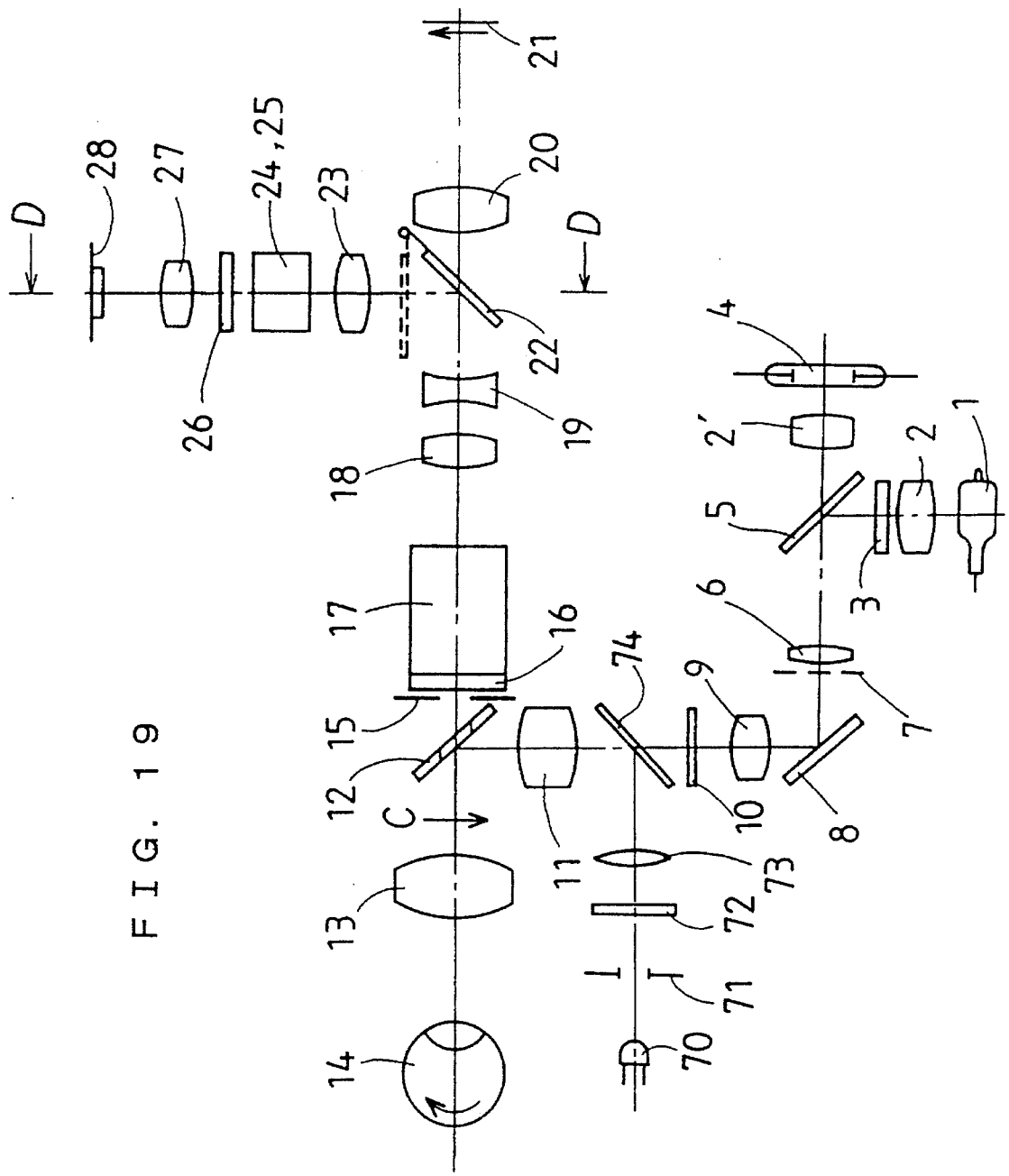
FIG. 19 is a schematic side view of the optical systems of a stereoscopic retinal camera in a third embodiment according to the present invention.

In a rough alignment by an examiner while observing picture images on a TV monitor, if the mydriasis diameter of an eye being observed is small as shown in FIG. 16 (a), and/or if photographing portion is dislocated from the center of posterior pole of the fundus as shown in FIG. 16 (b), the photographing optical axis is deviated and one of the two stereo photographing luminous flux is eclipsed accordingly, so that one picture screen of the TV monitor becomes dim as shown in FIG. 18. When such a phenomenon is observed, the camera is shaken in a lateral direction with respect to the pupil of the examinee's eye so that right and left pictures are substantially uniformly bright on the TV monitor.

Figure 17:
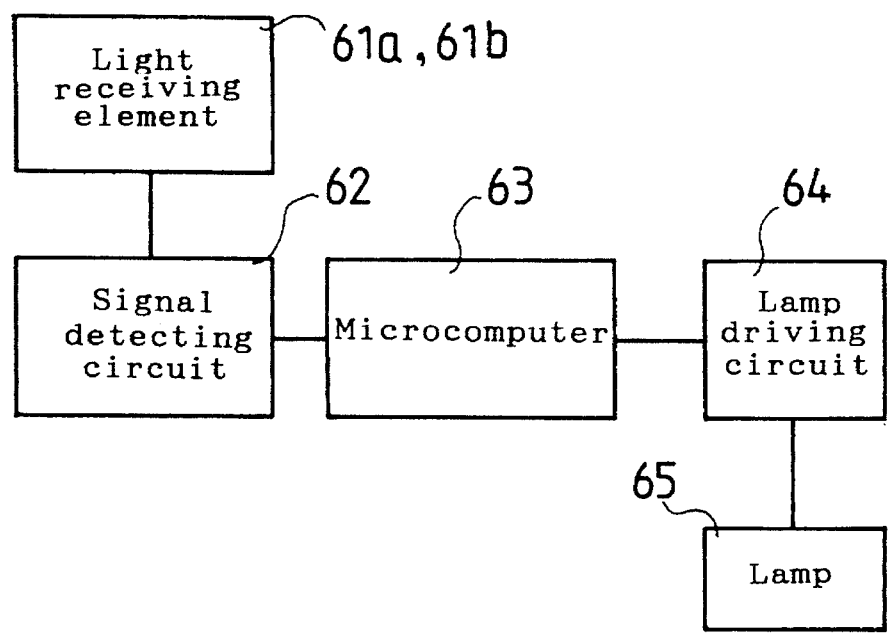
FIG. 17 is a block diagram of the electric system for detecting video signal strength.

After fine adjustment of alignment, further, uniformity of brightness of the pictures on the level imperceptible on the TV monitor is detected through the electric system as shown in FIG. 17. In the electric system, signals of light quantity which are incident to the light receiving elements 61a and 61b is detected at a signal detecting circuit 62 and transmitted to a microcomputer 63. When received the signals, the microcomputer 63 judges whether a difference of video signal strength between the light receiving elements 61a and 61b is within a predetermined value (acceptable value). If the difference value is within a predetermined value, the microcomputer 63 drives a lamp driving circuit 64 to turn on a lamp 65 which is provided near the TV monitor, thereby to inform a photographer that alignment condition is proper. When seeing the lamp 65 lighting, the photographer finishes fine alignment for balance of video signal strength in the right and left pictures.

In a third embodiment, a stereoscopic retinal camera comprises similar components to the first embodiment, except for an index projecting system and an index light detecting system. Explanation of the similar components will accordingly be omitted in the present embodiment.

Figure 21:
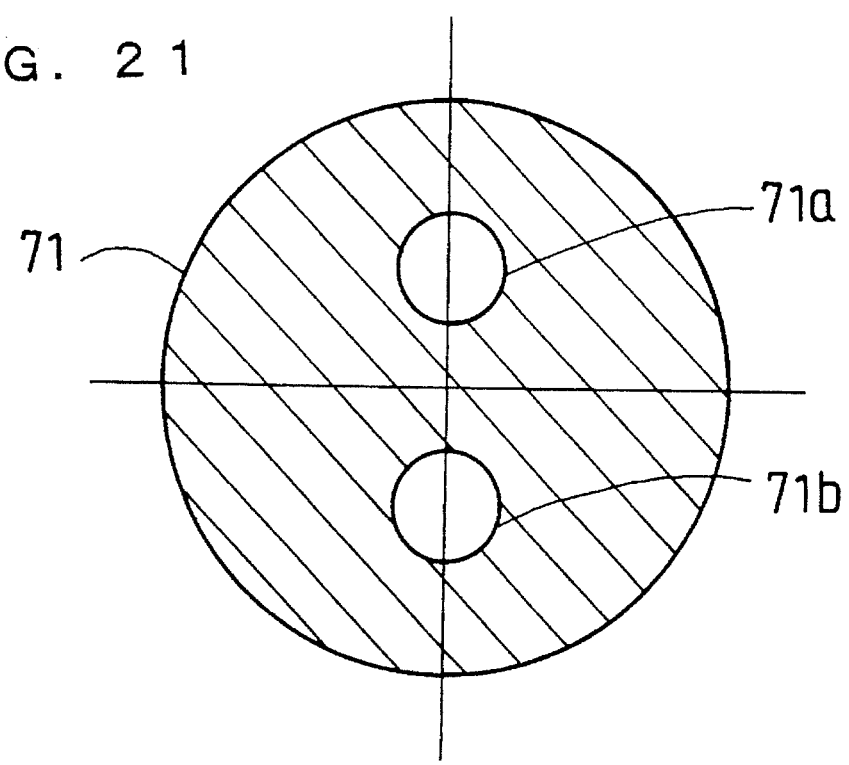
FIG. 21 is a schematic view of a two-hole diaphragm 71 of FIG. 19.
Figure 22:
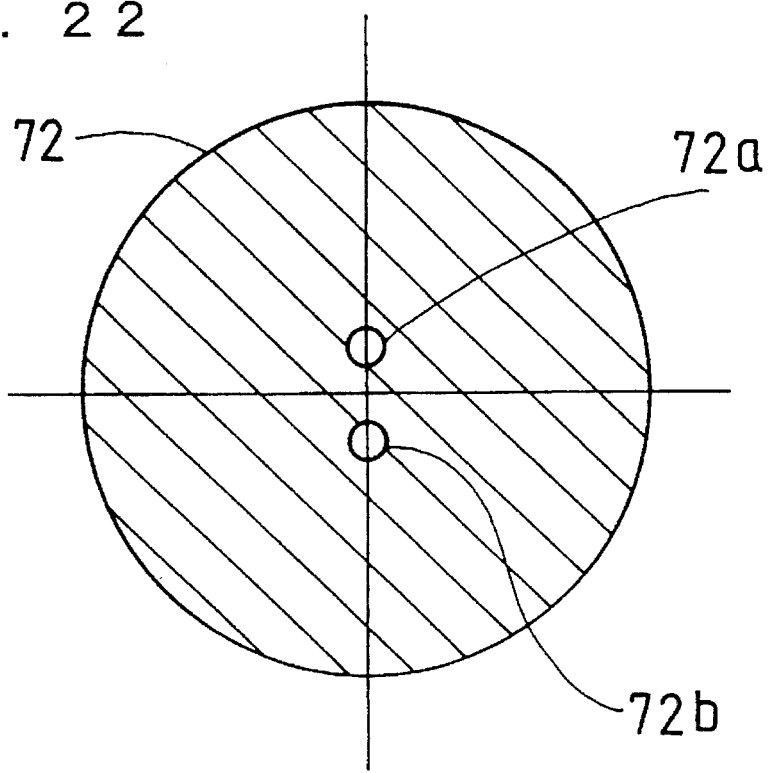
FIG. 22 is a schematic view of an index plate 72 of FIG. 19.

The index projecting system comprises of two light sources 70a and 70b which both emit light beam of a wavelength different from the same of light beam emitted by the observing illumination light source, a two-hole diaphragm 71 (referring to FIG. 21) to divide luminous flux for projecting index into two light beams, an index plate 72 (referring to FIG. 22), an index projecting auxiliary lens 73, and a dichroic mirror 74. The dichroic mirror 74 is disposed on a light path between the index plate 10 and the relay lens 11 of the illuminating optical system, capable of transmitting illumination light of the observing and the photographing optical systems and of reflecting index projecting light emitted by the light sources 70a and 70b so as to be directed along a common light path with the illumination optical systems to the eye 14.

Figure 20:
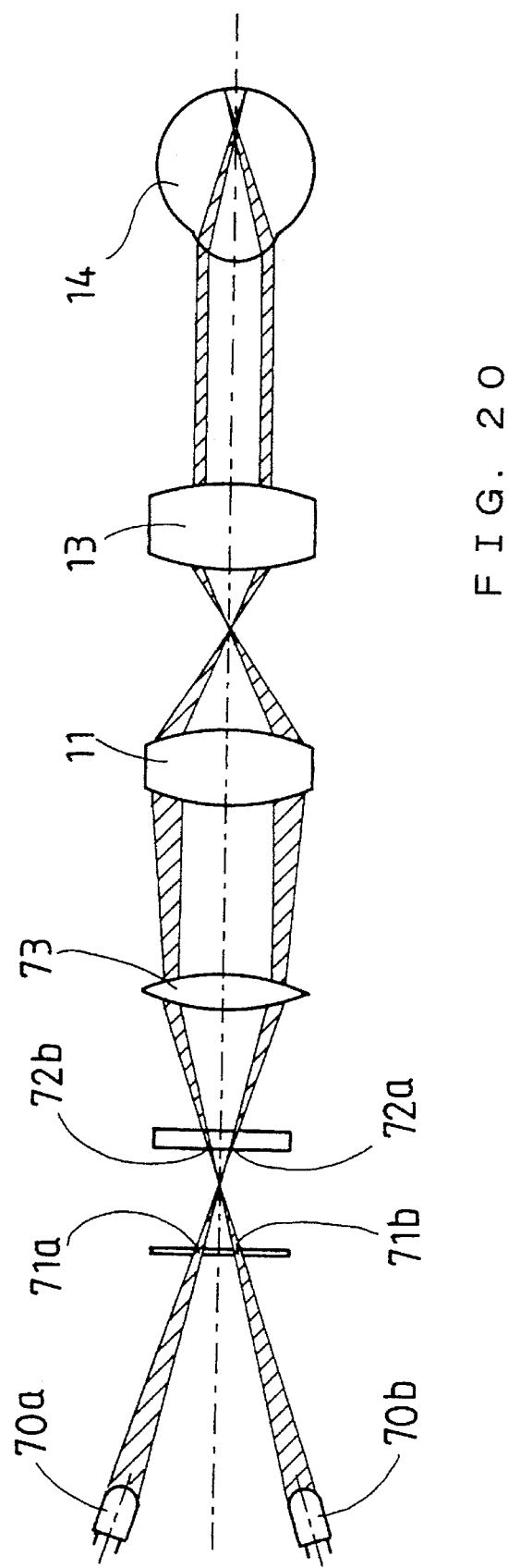
FIG. 20 is a plane view of an index projecting system of a stereoscopic retinal camera of FIG. 19, in which a dichroic mirror 74 and a perforated mirror 12 are omitted.

Function of the index projecting optical system will be described hereinafter, referring to FIG. 20 which shows an index projecting system including a common optical system with the illumination optical system, wherein the dichroic mirror 74 and the perforated mirror 12 are omitted from FIG. 20.

Figure 23:
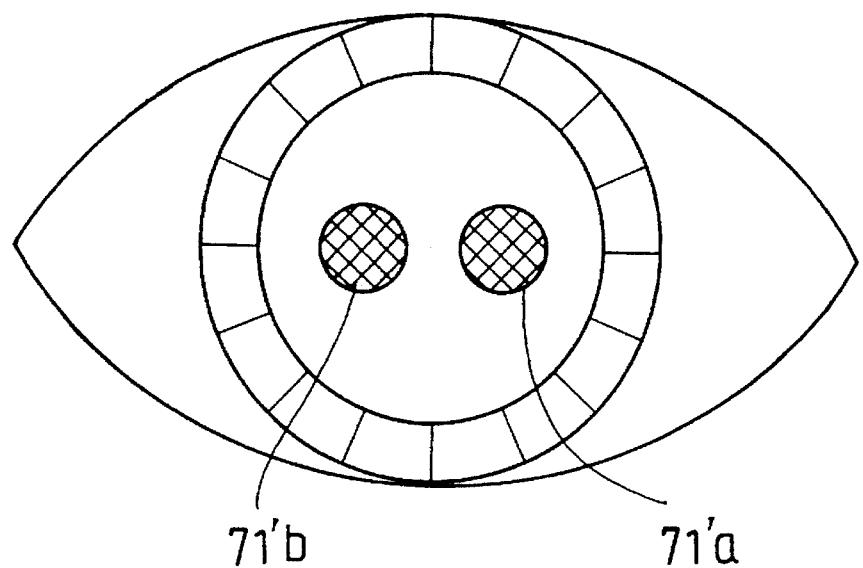
FIG. 23 is a schematic view of showing an image of the two-hole diaphragm 71 on the pupil of the eye.
Figure 24:
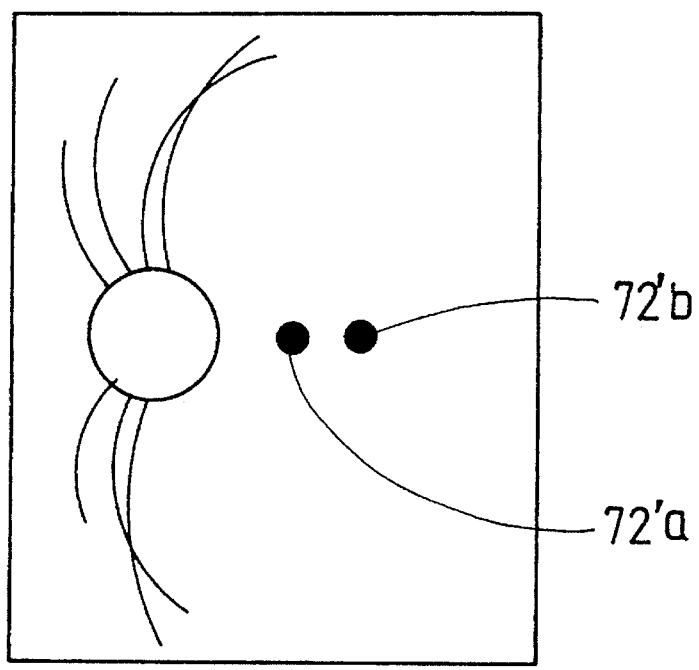
FIG. 24 is a schematic view of showing an image of the index 72 on the fundus.

The two-hole diaphragm 71 and the pupil of the eye 14, as well as the index plate 72 and the fundus of the eye 14, are disposed in a substantially conjugate relationship with each other. As shown in FIG. 20, index projecting luminous flux emitted by the light source 70a is transmitted through only the aperture 71a of the diaphragm 71 shown in FIG. 21 to illuminate the index 72a of the index plate 72 shown in FIG. 22. Similarly, index projecting luminous flux emitted by the light source 70b is transmitted through only the aperture 71b to illuminate the index 72b. Images 71'a and 71'b of the apertures 71a and 71b of the two-hole diaphragm 71 are produced on the pupil of the eye 14 as shown in FIG. 23, and images 72'a and 72'b of the indexes 72a and 72b are produced on the fundus of the eye 14 as shown in FIG. 24.

Figure 25:
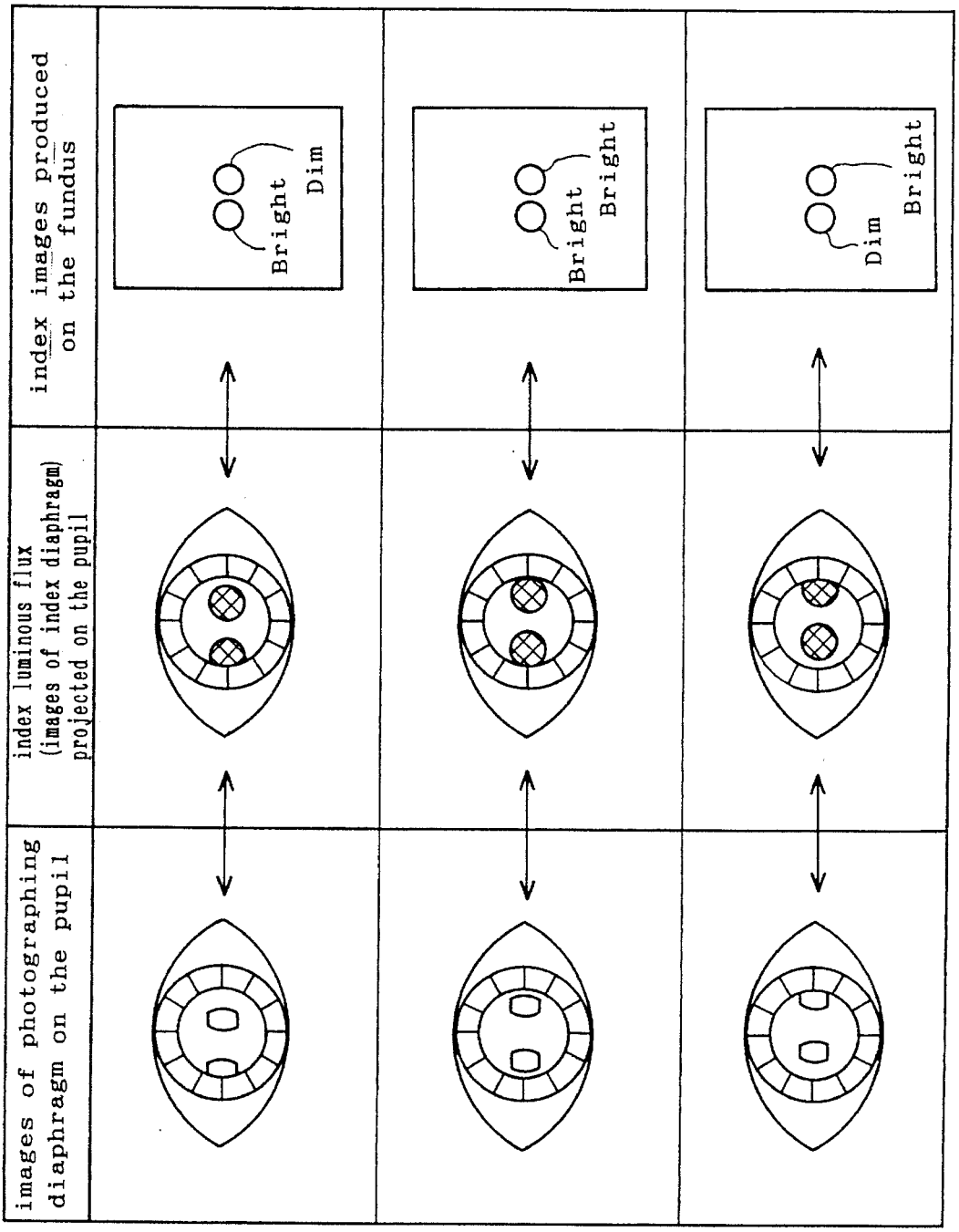
FIG. 25 is a relative diagram among images of the photographing diaphragm, images of luminous flux of index, both of which are projected on pupil, and balance of video signal strength of index light projected on the fundus.

The two-hole diaphragm 71 is constructed so that a center distance between images 71'a and 71+b is equal to same of the two-hole diaphragm 15 of the photographing optical system and each diameter of the images 71'a and 71'b is larger than or equal to the images of the two-hole diaphragm 15. In a case where the light path along which a photographing light beam is transmitted to the fundus is not in a center of the pupil of the eye, index projecting light beams are partially eclipsed by the pupil. One of the index images 72'a and 72'b formed on the fundus, which is produced by the eclipsed light beam, becomes dimmer than another image, so that this causes imbalance of video signal strength between the images 72'a and 72'b. In FIG. 25, shown is a diagram of illustrating balance of vide signal strength between the index images produced on the fundus, related to images of photographing diaphragm and index light on the pupil.

Figure 26:
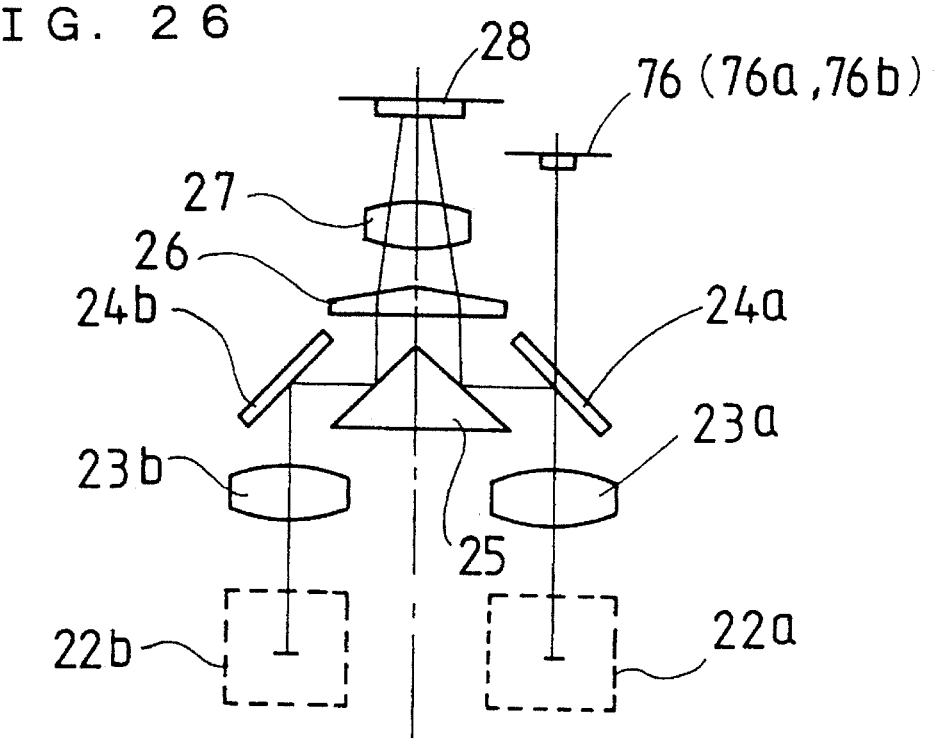
FIG. 26 is a schematic sectional view on line D—D of the observing optical system of the stereoscopic retinal camera of FIG. 19.

An observing optical system of the third embodiment is shown in FIG. 26. The observing optical system also comprises the similar components between the return mirrors 22 (22a, 22b) and the image sensor 28 to that of FIGS. 3 and 15, but the numeral 24a shows a dichroic mirror which serves to deflect luminous flux inwardly to shorten a distance and also to selectively partially transmit luminous flux reflected by the fundus and the numeral 24b shows a reflecting mirror for deflecting luminous flux inwardly to shorten a distance between the two luminous flux. And a light receiving element 76 is provided to receive the luminous flux which passed through the mirror 24a.

Figure 27:
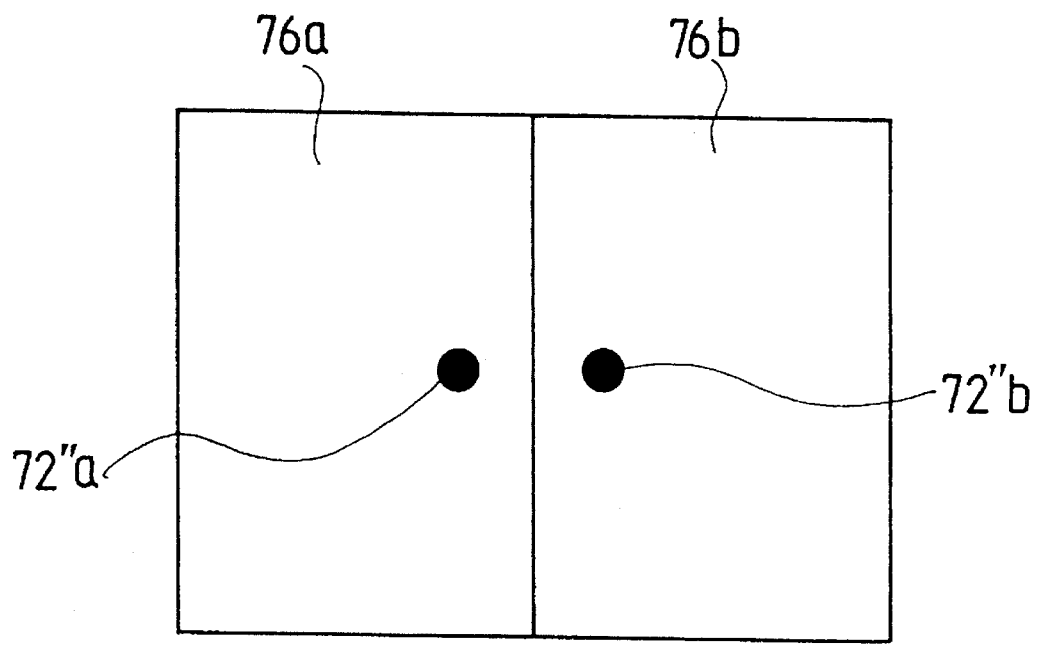
FIG. 27 is a schematic view of image forming elements 76a and 76b receiving index images formed on the fundus.

The index light receiving system shares a common components between the relay lens 11 and the dichroic mirror 24 (only 24b) with the observing optical system. Luminous flux passed through the dichroic mirrors 24a is directed to the light receiving element 76 (76a, 76b). The light receiving element 76, which is disposed in a substantially conjugate relationship with the film 21, receives the index images 72'a and 72'b formed on the fundus, thereby to form images 72"a and 72"b on the light receiving element. The optical system further provides a function capable of comparing video signal strength between the index images 72"a and 72"b formed on the light receiving elements. For instance, it is conceivable that, as shown in FIG. 27, a light receiving element is divided into two elements to form an index image 72"a at a light receiving section 76a and another index image 72"b at another light receiving section 76b respectively. Video signal strength received at the light receiving sections are directed into a predetermined processing.

Assuming that X represents the video signal strength received at the light receiving element 76a and Y represents same at the light receiving element 76b, comparison between X and Y provides the following result.

| (1) | (2) | (3) | (4) |
|-----|-----|-----|-----|
| X > Y | 72'a > 72'b | 71'b being eclipsed | left |
| X = Y | 72'a = 72'b | no eclipse | complete alignment |
| X < Y | 72'a < 72'b | 71'a being eclipsed | right |

(1) Video signal strength at light receiving elements.
(2) Brightness of index images produced on fundus.
(3) Luminous flux being eclipsed by pupil.
(4) Alignment direction to shift the apparatus.

Figure 28:
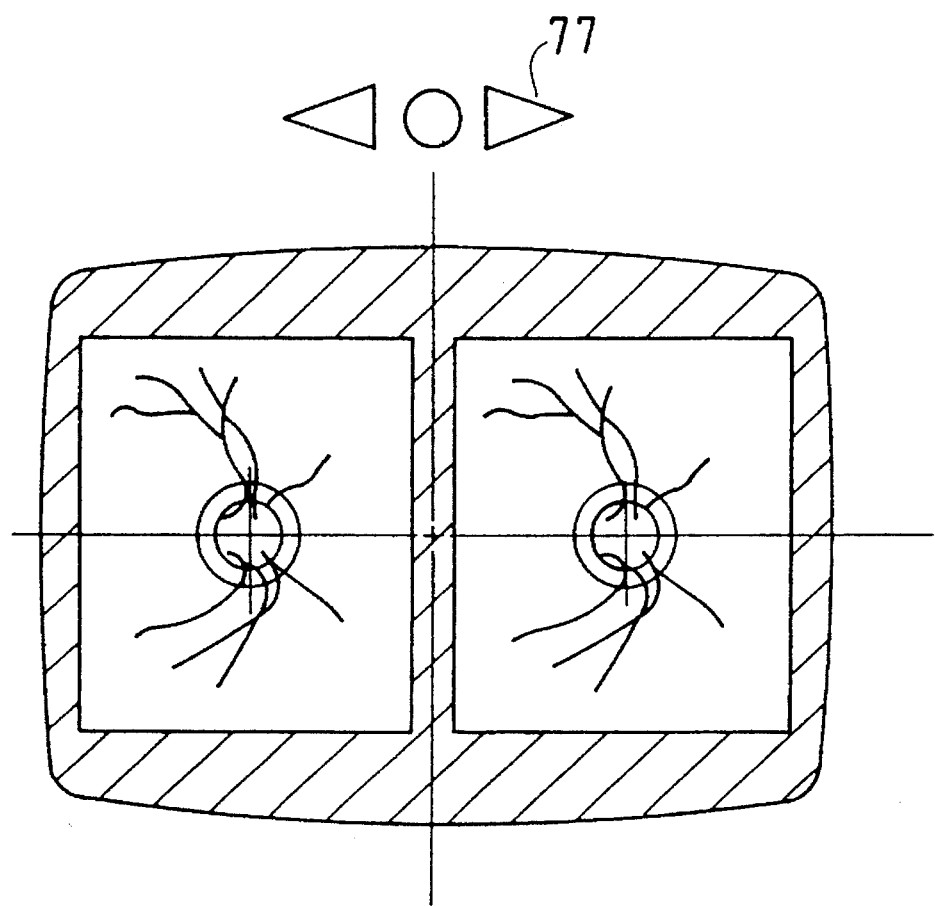
FIG. 28 is a schematic view of showing an example of the images of the fundus photographed with a TV camera and displayed on a TV monitor screen, and a mark indicating alignment direction.

In accordance with the result, the apparatus can be aligned properly with respect to the center of the pupil. More specifically, based on the compared result, either mark (denoted by 77 in FIG. 28) is lightened to inform an alignment direction of the apparatus to the examiner.

Operation of the apparatus as described above, excepting manual operation, is controlled by control system including a microcomputer provided inside the apparatus.

The present invention may be embodied in other specific forms without departing from the spirit or essential characteristics thereof.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A stereoscopic retinal camera comprising a photographic optical system capable of photographing a pair of stereoscopic fundus images by dividing a light beam reflected by the fundus of an examinee's eye into two light beams through a two-hole diaphragm, the camera comprising;

an illuminating optical system for illuminating the fundus of an examineess eye;

an observing optical system for observing the fundus illuminated by said illuminating optical system;

a detecting optical system for detecting the luminous flux reflected by the fundus and then directed into said observing optical system; and alignment judging means for judging whether a difference in balance of video signal strength between a pair of the fundus images is within a predetermined allowable range based on the luminous flux detected by said detecting optical system to thereby determine whether alignment is proper.

2. The stereoscopic retinal camera according to claim 1, wherein said observing optical system comprises a pair of optical systems to observe a pair of the fundus images, and said detecting optical system comprises light splitting means disposed in each light path of said pair of optical systems, condenser lenses and light receiving elements for detecting luminous flux condensed by said condenser lens.

3. The stereoscopic retinal camera according to claim 1, wherein said detecting optical system includes imaging means disposed in a substantially conjugate relationship with the fundus of the examinee.

4. The stereoscopic retinal camera according to claim 3, wherein said imaging means is used in common with the observing optical system.

5. The stereoscopic retinal camera according to claim 1, further comprising means for projecting index light to the fundus of the examinee's eye for measuring balance of video signal strength.

6. The stereoscopic retinal camera according to claim 5, wherein said index light projecting means comprises an index plate disposed in a substantially conjugate relationship with the fundus and a two-hole diaphragm disposed in a substantially conjugate relationship with the pupil of the examinee's eye, whereby two index luminous flux are directed through a peripheral portion of the pupil to the fundus.

7. A stereoscopic retinal camera comprising a photographic optical system capable of photographing a pair of stereoscopic fundus images by dividing a light beam reflected by the fundus of an examinee's eye into two light beams through a two-hole diaphragm, the camera comprising:

an illuminating optical system for illuminating the fundus of an examinee's eye;

an observing optical system for observing the fundus illuminated by said illuminating optical system;

a detecting optical system for detecting the luminous flux reflected by the fundus and then directed into said observing optical system; and judging means for judging balance of video signal strength between a pair of the fundus images based on the detected result by said detecting optical system;

wherein said detecting optical system includes am imaging element located in a conjugate relationship with the fundus# and said judging means includes comparing means for comparing accumulative amount of video signal strength of imaging elements on a predetermined scanning line.

8. A stereoscopic retinal camera comprising a photographic optical system capable of photographing a pair of stereoscopic fundus images by dividing a light beam reflected by the fundus of an examinee's eye into two light beams through a two-hole diaphragm, the camera comprising:

an illuminating optical system for illuminating the fundus of an examinee's eye;

an observing optical system for observing the fundus illuminated by said illuminating optical system;

a detecting optical system for detecting the luminous flux reflected by the fundus and then directed into said observing optical system;

judging means for judging balance of video signal strength between a pair of the fundus images based on the detected result by said detecting optical system; and means for projecting index light to the fundus of the examinee's eye for measuring balance of video signal strength wherein said index light projecting means comprises an index plate disposed in a substantially conjugate relationship with the fundus and a two-hole diaphragm disposed in a substantially conjugate relationship with the pupil of the examinee's eve, whereby two index luminous flux are directed through a peripheral portion of the pupil to the fundus; and wherein said two-hole diaphragm has apertures so that images of the apertures on the pupil of the eye are formed at approximately the same interval as images of the apertures of the two-hole diaphragm for the photographing optical system on the pupil, and each image is the same dimension as or larger than that of the two-hole diaphragm for the photographing optical system.

9. A stereoscopic retinal camera comprising a photographing optical system capable of photographing a pair of stereoscopic fundus images by dividing a light beam reflected by the fundus of an examinee's eye into two light beams through a two-hole diaphragm, the camera comprising;

an illuminating optical system for illuminating the fundus of an examinee's eye;

an observing optical system for observing the fundus illuminated by said illuminating optical system;

a detecting optical system for detecting the luminous flux reflected by the fundus and then directed into said observing optical system;

judging means for alignment judging balance of video signal strength between a pair of fundus images based on the detected result by said detecting optical system; and indicating means for indicating a direction to move the camera based on a result at said judging means.

* * * * *